United States Patent
Nelson (10) Patent No.: US 10,695,183 B2
(45) Date of Patent: Jun. 30, 2020

(54) AUGMENTS AND METHODS OF IMPLANTING AUGMENTS

(71) Applicant: Charles L. Nelson, Vorhees, NJ (US)

(72) Inventor: Charles L. Nelson, Vorhees, NJ (US)

(*) Notice: Subject to any disclaimer, the term of this patent is extended or adjusted under 35 U.S.C. 154(b) by 217 days.

(21) Appl. No.: 15/921,455

(22) Filed: Mar. 14, 2018

(65) Prior Publication Data

US 2018/0263672 A1 Sep. 20, 2018

Related U.S. Application Data

(60) Provisional application No. 62/471,066, filed on Mar. 14, 2017.

(51) Int. Cl.
*A61F 2/30* (2006.01)
*A61F 2/46* (2006.01)
*A61F 2/38* (2006.01)

(52) U.S. Cl.
CPC .......... *A61F 2/30734* (2013.01); *A61F 2/461* (2013.01); *A61F 2/4609* (2013.01); *A61F 2/3859* (2013.01); *A61F 2/46* (2013.01); *A61F 2/4603* (2013.01); *A61F 2002/30738* (2013.01)

(58) Field of Classification Search
CPC .... A61F 2/30734; A61F 2/3859; A61F 2/389; A61F 2/46; A61F 2/4603; A61F 2/4609; A61F 2/461; A61F 2002/30736; A61F 2002/30738
See application file for complete search history.

(56) References Cited

U.S. PATENT DOCUMENTS

| | | | |
|---|---|---|---|
| 5,387,241 A | | 2/1995 | Hayes |
| 5,549,692 A | * | 8/1996 | Hauser ............... A61F 2/30734 623/22.3 |
| 9,526,513 B2 | * | 12/2016 | Collazo ............. A61B 17/1764 |
| 9,668,758 B2 | * | 6/2017 | Collazo ............. A61F 2/30724 |
| 9,907,657 B2 | * | 3/2018 | Fonte .................... A61L 27/306 |
| 9,907,664 B2 | * | 3/2018 | Blaylock ........... A61B 17/1675 |
| 2004/0162619 A1 | * | 8/2004 | Blaylock ........... A61B 17/1764 623/20.16 |
| 2004/0172137 A1 | * | 9/2004 | Blaylock ............. A61F 2/30771 623/20.16 |
| 2005/0143837 A1 | * | 6/2005 | Ferree ................. A61B 17/164 623/23.25 |

(Continued)

OTHER PUBLICATIONS

Zimmer Trabecular Metal Femoral and Tibial Cone Augments, Product Literature, 2008, 6 pages.

(Continued)

*Primary Examiner* — Eric S Gibson
(74) *Attorney, Agent, or Firm* — McCarter & English, LLP (57) ABSTRACT

Exemplary embodiments are directed to an augment and methods of implanting an augment. The methods include inserting the augment into a bone cavity of a bone of a host. The augment includes a body with an outer surface and at least one hole preformed in the body. The method includes introducing a fastener from an outer surface of the bone into a hole formed in the bone and engaging the fastener with the hole of the bone. The method includes passing the fastener through the hole of the bone. The method includes introducing into and engaging the fastener with the at least one hole in the body of the augment to fixate the augment within the bone cavity.

15 Claims, 6 Drawing Sheets

(56) References Cited

U.S. PATENT DOCUMENTS

| | | | | |
|---|---|---|---|---|
| 2012/0310361 A1* | 12/2012 | Zubok | A61F | 2/30734 |
| | | | | 623/20.32 |
| 2014/0276882 A1* | 9/2014 | Collazo | A61B | 17/164 |
| | | | | 606/96 |
| 2014/0277528 A1* | 9/2014 | Mines | A61F | 2/3859 |
| | | | | 623/20.16 |
| 2015/0157462 A1* | 6/2015 | Ek | A61F | 2/4081 |
| | | | | 623/19.11 |
| 2016/0184103 A1* | 6/2016 | Fonte | A61L | 27/306 |
| | | | | 623/23.5 |
| 2017/0135819 A1* | 5/2017 | Collazo | A61B | 17/1675 |
| 2018/0125662 A1* | 5/2018 | Dees | A61F | 2/30734 |
| 2018/0193152 A1* | 7/2018 | Bauer | A61F | 2/34 |
| 2018/0200061 A1* | 7/2018 | Bauer | A61F | 2/30734 |
| 2018/0263672 A1* | 9/2018 | Nelson | A61B | 17/8061 |
| 2018/0296350 A1* | 10/2018 | Hamzey | A61B | 17/7291 |
| 2019/0070008 A1* | 3/2019 | Bauer | A61F | 2/30734 |
| 2019/0105162 A1* | 4/2019 | Zhang | A61F | 2/3672 |

OTHER PUBLICATIONS

Zimmer Modular Augments, https://www.researchgate.net/figure/TM-modular-augments-courtesty-of-Zimmer-Warsah-Ind-US-Preference-between-wedges-and_fig2_221923199; Mar. 8, 2018.

* cited by examiner

AUGMENTS AND METHODS OF IMPLANTING AUGMENTS

CROSS-REFERENCE TO RELATED APPLICATIONS

This application claims the benefit of U.S. Provisional Patent Application No. 62/471,066, which was filed on Mar. 14, 2017. The entire content of the foregoing provisional patent application is incorporated herein by reference.

TECHNICAL FIELD

The present disclosure relates to augments and methods of implanting augments that provide enhanced fixation to bone and/or soft tissue.

BACKGROUND

Revision total knee or hip replacement is becoming increasingly common with the success of the procedure, the aging population, and more frequent use in younger individuals. Management of bone loss and optimizing stability and function are important challenges faced during revision total knee and hip replacement. Porous or porous coated metal knee cones or acetabular augments, custom porous coated cups, and acetabular reconstruction cages are available in the industry to accommodate areas of bone loss. Short and intermediate-term studies demonstrate acceptable outcomes in the setting of bone loss during revision total knee or hip replacement using traditional porous cones and augments. Particularly, these cones or augments allow biologic fixation with bone healing directly to the porous augment, porous cone or sleeve, replacing areas of bone loss while enhancing fixation and allowing restoration of a more normal knee joint line or more normal hip center of rotation.

Traditional porous cones are generally inserted into the area of bone loss and centered within the cavity by the remaining bone, the cone maintaining its position via a friction fit. If bone loss in the host occurs only on one side of the cavity, removal of healthy bone is performed on the opposing side to ensure proper centering of the cone within the cavity. Upon forming the cavity and introducing the cone, stable contact between the remaining bone and the cone may not occur due to the configuration of the cavity. Such failed contact can result in extended time for bone in-growth or failure of bone in-growth at certain surfaces of the cone. Traditional cones also do not provide a means for attachment of avulsed or fractured bone with important ligament and/or tendon attachments, such as the femoral epicondyle(s) or tibial tubercle.

Thus, a need exists for improved augments that can be introduced into differently sized cavities without extensive removal of healthy bone, augments that ensure direct and/or stable contact with the remaining bone of the cavity, and augments that reliably attach important fractured metaphyseal bone segments. These and other needs are addressed by the augments and methods of the present disclosure.

SUMMARY

In accordance with embodiments of the present disclosure, an exemplary method of implanting an augment is provided. As discussed herein, augments refer to any implantable device, such as a cone, sleeve, acetabular augment, or the like. The method includes at least partially inserting the augment into a bone cavity of a bone of a host. The augment includes a body with an outer surface and at least one hole preformed in the body. The method includes introducing a fastener from an outer surface of the bone into a hole formed in the bone and engaging the fastener with the hole of the bone. The method includes passing the fastener through the hole of the bone. The method includes introducing into and engaging the fastener with the at least one hole in the body of the augment to fixate the augment within the bone cavity.

The method includes forming the bone cavity in the bone of the host in preparation for implantation of the augment. The method includes forming the hole in the bone. The hole extends from the outer surface of the bone into the bone cavity. Engaging the fastener with the at least one hole in the body of the augment urges the augment towards an inner surface of the bone cavity, and fixates the augment to the inner surface of the bone cavity.

In some embodiments, the bone can be at least one of a femur, a tibia, or an acetabulum. In some embodiments, the augment can be formed from at least one of a metal, a non-metal, a biodegradable material, combinations thereof, or the like. The body of the augment can be porous to allow for bone and/or tissue in-growth over time. In some embodiments, the body can be flexible such that during fixation with the fastener, the body at least partially conforms to the surrounding inner surface of the bone cavity to improve contact between the augment and bone.

In some embodiments, the augment can be conical in shape including a hollow inner cavity. The at least one hole in the body of the augment extends from the outer surface into the hollow inner cavity. In some embodiments, the at least one hole in the body of the augment can be threaded. In such embodiments, the method includes engaging threads of the fastener with complementary threads of the at least one hole in the body of the augment.

In some embodiments, at least a portion of the body of the augment can include a deformable material. For example, the at least one hole can be preformed in the deformable material of the augment. In some embodiments, the augment can include the deformable material in an area immediately surrounding the at least one hole of the augment. In such embodiments, engaging the fastener with the at least one hole in the body of the augment can include deforming the deformable material of the augment with threads of the fastener to fixate the fastener to the augment.

In accordance with embodiments of the present disclosure, an exemplary method of implanting an augment is provided. The method includes forming a bone cavity in a bone of a host, and forming a hole in the bone. The hole extends from an outer surface of the bone into the bone cavity. The method includes inserting the augment into the bone cavity of the bone. The augment includes a body with an outer surface and at least one hole preformed in the body. The method includes introducing a fastener from the outer surface of the bone into the hole of the bone and engaging the fastener with the hole of the bone. The method includes passing the fastener through the hole of the bone. The method includes introducing into and engaging the fastener with the at least one hole in the body of the augment to fixate the augment within the bone cavity.

In accordance with embodiments of the present disclosure, an exemplary augment configured to be implanted into a bone cavity and fixated within the bone cavity with at least one fastener is provided. The augment includes a body including an outer surface and a hollow inner cavity. The augment includes at least one hole preformed in the body extending from the outer surface into the hollow inner cavity. The at least one hole includes threads complementary to threads of the fastener. The body is configured and dimensioned to be inserted within the bone cavity and fixated against an inner surface of the bone cavity with the at least one fastener.

In some embodiments, the body can be at least partially porous. In some embodiments, the body can be flexible to allow for improved contact between the augment and bone during fixation. In some embodiments, the augment can be formed from a metal, a non-metal, a biodegradable material, combinations thereof, or the like. In some embodiments, at least a portion of the body around the at least one hole can include a deformable material.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed augments and methods of implanting augments, reference is made to the accompanying figures, wherein.

DESCRIPTION OF EXEMPLARY EMBODIMENTS

In accordance with embodiments of the present disclosure, exemplary augments and methods of implanting augments are provided that enhance the attachment or fixation of the augments to bone without the need for excessive removal of healthy bone. As noted above and used herein, augments refer to any implantable device, such as a cone, sleeve, acetabular augment, or the like. In some embodiments, the augments can be porous coated, metal, non-metal and/or biodegradable cones or sleeves configured to be fixated to bone (e.g., with lagging screws or bolts). The exemplary augments ensure bone in-growth (e.g., biologic fixation) due to improved contact between the augment and the remaining bone. In some embodiments, the exemplary augments enhance attachment and fixation of important bone and soft tissue structures during revision or complex primary total knee replacement, particularly in the setting of bone loss or fracture using augments positioned within the metaphysis or diaphysis of the distal femur or proximal tibia. The augment can be attached or fixated to bone and/or soft tissue (e.g., epicondyles, collateral ligaments, tibial tubercle/patella tendon, or the like) with one or more lagging screws or bolts during insertion and implantation. The augments improve fixation in the setting of bone loss while allowing attachment of structures, such as the collateral ligaments or patellar tendon attachment, to optimize stability and function.

Porous or porous coated metal augments positioned within the metaphysis or diaphysis of the distal femur or proximal tibia include preformed, threaded holes to allow attachment of the augment to surrounding bone or soft tissue using lagging screws/bolts with or without washers. The threaded holes can be substantially central in location such that the screw first penetrates the bone prior to engaging the threaded hole of the augment. These screws/bolts can be placed to precisely engage the threaded hole of the augment with a drill guides, allowing for threading in to the most central aspect of the threaded hole. Passage of the screw/bolt through the bone and subsequent passage of the screw/bolt through the augment ensures that the augment is urged towards the inner surface of the bone cavity, resulting in substantially direct contact between the augment and the bone. In some embodiments, the augment can be formed from a flexible material such that the augment can conform to the inner surface of the bone cavity during urging and fixation of the augment.

In some embodiments, rather than preformed, threaded holes, the augment can include one or more portions formed from a deformable material such that the screw/bolt can be threaded through the deformable at any angle, while still urging the augment towards the inner surface of the bone cavity. In such embodiments, a hole having a smaller diameter than the screw/bolt can be formed in the deformable portion of the augment, with threading of the screw/bolt through the hole resulting in deformation that accommodates the screw/bolt. Over time, due to the improved contact between the bone and augment, the bone can heal to the porous surface by bone in-growth.

In some embodiments, the exemplary augments can be used to enhance fixation, substitution for bone loss, and establishment of a foundation in the setting of acetabular reconstruction during revision hip replacement surgery or complex primary hip replacement surgery. For example, the augment can be used in the setting of revision hip replacement when there is loss of superior and medial acetabular bone with a thin shelf of ilium around which the augment can be placed. In some embodiments, the augment can be used to enhance distal fixation into the ischium in the setting of bone loss. The acetabular augments or porous/coated acetabular reconstruction augments can be used to span bone loss or pelvic discontinuity (e.g., pelvic/acetabular fracture, non-union, or the like) during acetabular reconstruction during revision and complex primary hip replacement, including acetabular fractures and limb salvage for cancer. Thus, the augments can be used in a variety of settings, including Paprosky Type 3B (up and in) defects or pelvic discontinuities where bone loss extends further superiorly and more medially with limited bone medially to achieve screw fixation. For example, U-shaped metal augments allow for surrounding areas of bone loss and provide optimal fixation from the augment, into the bone, and back into threads pre-fabricated into the augment.

The augment provides a substantially U-shaped configuration or extensions from a porous cup or reconstruction cage to surround areas of bone loss. Metal or bio-degradable screws can be used to provide optimal fixation of the augment into bone, and back into threads or deformable material prefabricated into the augment, allowing for enhanced fixation of the screw into the medial portion of the augment. The threaded or deformable portion of the augment, present in the medial position of the U-shaped augment, can be targeted with a drill guide which attaches or threads into the lateral exposed portion of the U-shaped augment to ensure accurate targeting of the threads. The bottom portion of the U-shaped augment can be produced with varying degrees of flexibility to allow compression of the augment against bone when the screw is tightened. In the setting of custom porous or porous coated cups or reconstruction cages, the proximal and/or distal portions can include the U-shaped augment that allows for lagging screw fixation with similar targeting strategies.

Figure 1:
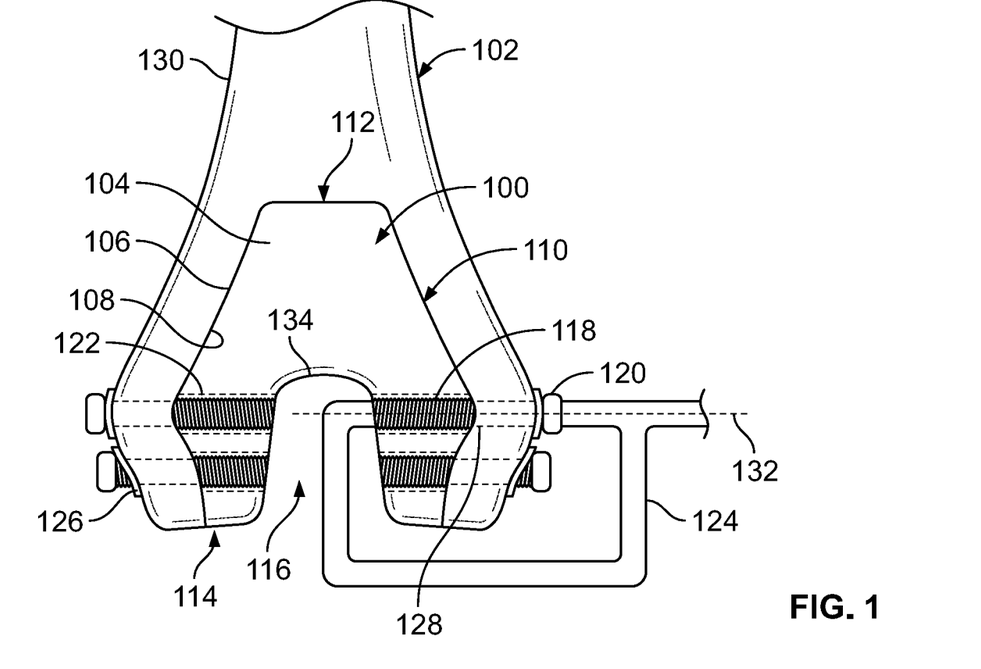
FIG. 1 is a diagrammatic, anterior-posterior view of a distal femur with an implanted exemplary augment in accordance with the present disclosure, having a configuration capable of attachment to both medial and lateral epicondyles.

With reference to FIG. 1, a diagrammatic, anterior-posterior view of an exemplary augment 100 implanted in a bone 102 (e.g., a distal femur) is provided. Particularly, FIG. 1 is a cross-sectional view that represents implementation and implantation of the augment 100. The augment 100 can be fabricated from a metal, non-metal, and/or biodegradable material. In some embodiments, the augment 100 can be fully porous to allow for bone in-growth. In some embodiments, the augment 100 can be porous coated, thereby also allowing for bone in-growth. For example, fully porous materials (such as three-dimensional printed materials or trabecular metal) allow for bone in-growth over time. As a further example, porous coated surfaces bonded or plasma sprayed onto a solid metal substrate can also be used to allow for bone in-growth over time. In some embodiments, the augment 100 can have a sleeve or cone-shaped configuration (e.g., a hollow interior and a substantially U-shaped cross-section, such as in FIG. 1).

The augment 100 includes a body 104 formed from the metal, non-metal, biodegradable, and/or porous material. In some embodiments, the body 104 can be flexible to allow for conformation of the body 104 to the bone 102 during implantation. The augment 100 includes an outer surface 106 configured to be in substantially direct contact with the inner surface 108 of a bone cavity 110 formed in the bone 102 of the patient. A top or distal end 112 of the augment 100 can have a substantially solid configuration (e.g., free of cavities, other than the porous structure), while a bottom or proximal end 114 of the augment 100 can include an opening leading into a hollow inner cavity 116. In some embodiments, the bottom surface 134 of the cavity 116 can define a rounded configuration.

The augment 100 includes one or more holes 118 preformed therein and extending from the outer surface 106 to the cavity 116. Although shown as passing through the entire thickness of the body 104 at the cavity 116, in some embodiments, the holes 118 can only partially extend through the thickness from the outer surface 106. For example, the holes 118 can pass halfway or three-fourths of the thickness starting from the outer surface 106 in the direction of the cavity 116. Although shown as only formed in the area of the body 104 having the cavity 116, in some embodiments, the augment 100 can include one or more holes 118 formed at or near the distal end 112. In some embodiments, the holes 118 can be substantially parallel to horizontal. It should be understood that FIG. 1 is a cross-sectional representation of the bone 102 and augment 100, and the holes 118 can be formed circumferentially in the augment 100 to ensure the desired fixation of the augment 100 to the bone 102.

In some embodiments, each hole 118 can be threaded to correspond with complementary threads of a fastener 120 (e.g., a lagging screw, bolt, or the like). In such embodiments, the hole 118 and the fastener 120 can be aligned using a drill guide 124 to ensure proper alignment and engagement of the threads. In some embodiments, rather than a pre-threaded hole, the augment 100 can include a deformable material 122 with an unthreaded hole 118 formed therein. For example, the augment 100 can include the deformable material 122 only around the unthreaded hole 118.

The deformable material 122 can be a polymeric, biodegradable material having sufficient strength and resistance to engage with the fastener 120 during threading. In such embodiments, the hole 118 can have a diameter dimensioned slightly smaller than the diameter of the fastener 120. The fastener 120 can be engaged with the hole 118 such that the threads of the fastener 120 deform the deformable material 122 (forming threads in the material 122) and engage with the augment 100. The fastener 120 can thereby be engaged with the augment 100 even if perfect alignment between the hole 118 and fastener 120 is not achieved. In some embodiments, the entire or substantially entire portion of the body 102 can be formed from the deformable material and unthreaded holes 118 can be preformed in the material for engagement with the fastener 120. It should be understood that the fastener 120 can be used with or without a washer 126. Although the fastener 120 head is shown angled relative to the bone 102 surface due to the angle of the bone 102, in some embodiments, a thicker washer 126 and/or a counter-sink in the bone 102 can be used to accommodate any angles in the bone 102 surface.

During implantation, the bone cavity 110 can be cleaned and prepared for introduction of the augment 100. Rather than removing healthy bone from the cavity 110, the augment 100 can be securely attached to the medial epicondyle with fasteners 120 without use of a symmetric augment 100 that would necessitate removal of healthy host bone 102 from the lateral femoral condyle. For example, for large, substantially symmetrical bone cavities 110, a symmetrical augment 100 can be used. As a further example, for partial, asymmetrical bone cavities 110, an asymmetrical augment can be used (see, e.g., FIG. 2). In some embodiments, the augment 100 can be trimmed or reconfigured (e.g., customized) based on the shape of the bone cavity 110. Holes 128 can be drilled within the bone 102 from the outer surface 130 to the inner surface 108 in positions corresponding with the holes 118 of the augment 100. In some embodiments, the holes 128 can be drilled within the bone 102 and subsequently holes 118 can be formed in the augment 102 based on the position of the holes 128. The augment 100 can be introduced into the cavity 110 and positioned in the desired location (e.g., aligning the holes 118, 128). The drill guide 124 can be used to accurately align the fastener 120 along an axis 132 corresponding with both holes 118, 128.

The fastener 120 is first threaded through and engaged with the bone 102. As the end of the fastener 120 passes through the inner surface 108 of the bone 102, the fastener 120 enters the hole 118 of the augment 100 at the outer surface 106, and threads through and engages with the hole 118 of the augment 100. The fastener 120 thereby secures the augment 100 to the inner surface 108 of the bone 102. Engagement of the fastener 120 with the hole 118 of the augment 100 can pull the augment 100 against the inner surface 108 of the cavity 110, ensuring a substantially direct contact between the augment 100 and bone 102 for bone in-growth. In some embodiments, the augment 100 can be formed from a flexible material that at least partially deforms to conform to the surface of the cavity 110 as the fastener 120 is engaged with the hole 118 of the augment 100. In some embodiments, the length of the fastener 120 can be selected such that the end of the fastener 120 substantially aligns with the inner surface of the cavity 116 (e.g., without protruding into the cavity 116).

Although referred to as bone 102, it should be understood that the augment 100 can be fixed to bone and the attached soft tissue structures to assist in setting of revision total knee replacement or complex primary knee replacement, especially in the setting of fracture. The fasteners 120 provide enhanced fixation of the epicondyles (collateral ligaments) and/or tibial tubercle/patella tendon attachment via insertion into the holes 118 of the augment 100, thereby optimizing knee stability and extensor mechanism function. The use of fasteners 120 with the holes 118 in the augment 100 can lead to improved fixation of the augment 100 to surrounding bone 102, leading to improved long-term fixation and lower rates of loosening.

Figure 2:
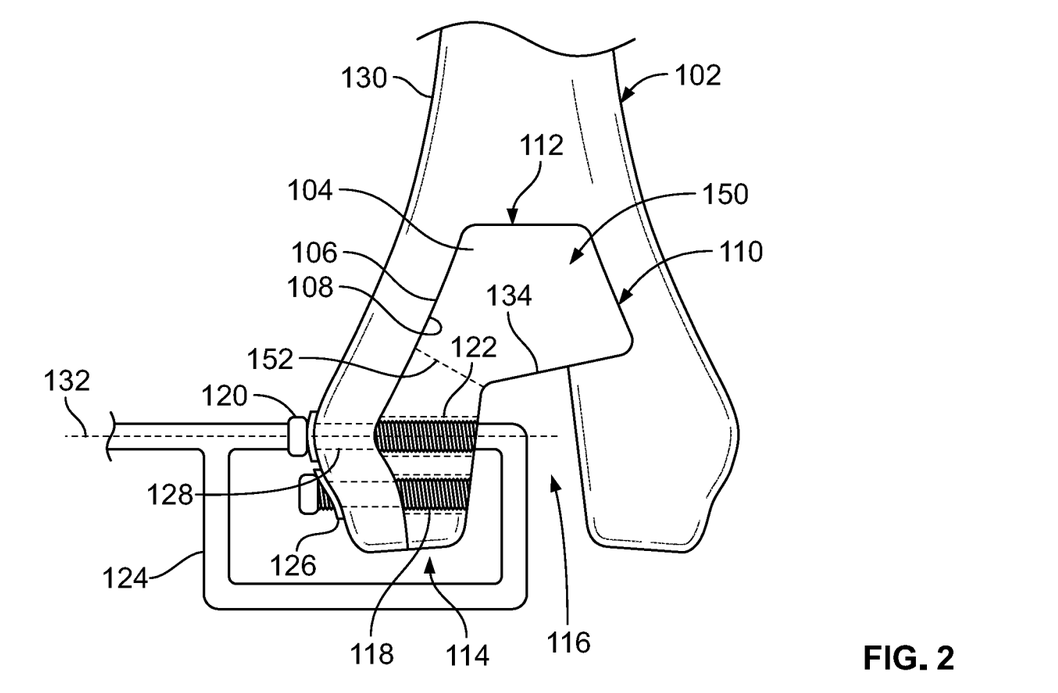
FIG. 2 is a diagrammatic, anterior-posterior view of a distal femur with an implanted exemplary augment in accordance with the present disclosure, having a configuration capable of attachment to a single, medial epicondyle.

Still with reference to FIG. 1, attachment of the augment 100 is shown to both the medial and lateral femoral epicondyles, including the attached collateral ligaments. Although an augment 100 having both epicondyles is shown, in some embodiments, the augment 100 can be reconfigured or provided in an alternative shape, e.g., a unicondylar porous augment as shown in FIG. 2. The number of holes 118 available can vary based on the size of the augment 100. Generally, at least two holes 118 can be used for rotational stability of the augment 100 within the cavity 110. The holes 118 can be proximal or distal to one another (as shown), anterior or posterior to one another, combinations thereof, or the like. Once the augment 100 has been attached and fixed to the surrounding bone 102 and/or soft tissue, the stemmed femoral prosthesis can be inserted with or without bone cement.

FIG. 2 is a diagrammatic, anterior-posterior view of an exemplary augment 150 implanted within a bone cavity 110. The augment 150 can be substantially similar in structure and function to the augment 100, except for the distinctions noted herein. Same reference numbers are therefore used to refer to same structures. Rather than securing the augment 100 to both medial and lateral epicondyles, the augment 150 is configured for attachment to only the medial epicondyle. Thus, the augment 150 defines a substantially L-shaped cross-section. In some embodiments, the bottom surface 134 of the cavity 116 can define an angled, linear configuration.

The augment 150 is attached to the medial femoral epicondyles including the attached medial collateral ligament. Once the augment 150 is attached and fixed to the surrounding bone 102 and/or soft tissue, the stemmed femoral prosthesis can be inserted with or without bone cement. The dashed line 152 represents the line at which a partial metaphyseal augment 150 ends. For example, rather than having a substantially L-shaped configuration, in some embodiments, the augment 150 can include only the portion below the dashed line 152 (e.g., a substantially linear, vertical extension). In such instances, there is no bone on the central side of the augment 150 to provide support, and the fasteners 120 are needed to provide stability via attachment to the adjacent bone 102. FIG. 2 therefore shows both the partial (medial or lateral only) metaphyseal only augment 150, as well as the potentially partial (medial or lateral) metaphyseal/diaphyseal augment 150. The augment 150 can be used where the bone 102 has healthy bone remaining on one side of the bone cavity 110, allowing for introduction and implantation of the augment 150 without removing the healthy bone. The augment 150 is secured to only one side (or along a partial radial edge) of the bone 102.

Figure 3:
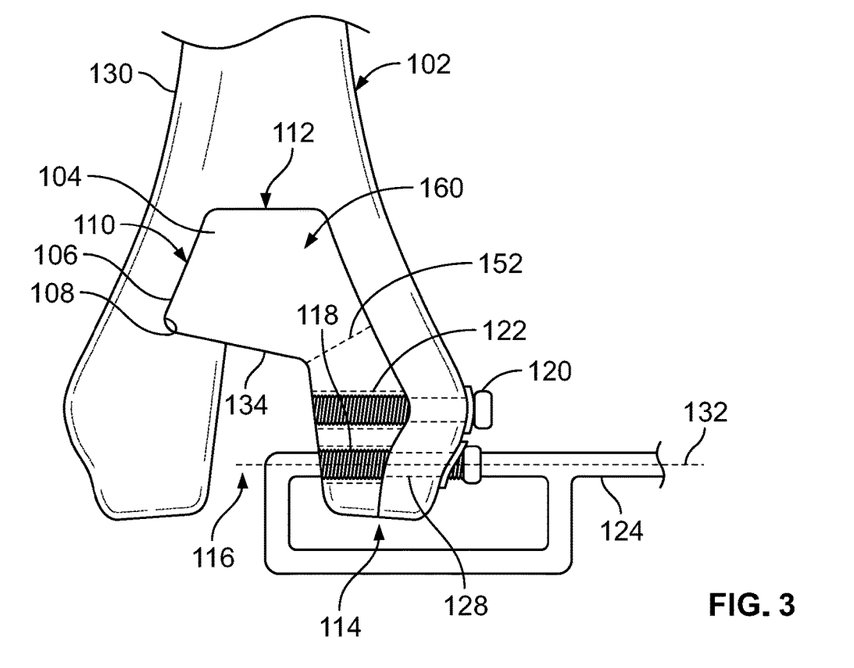
FIG. 3 is a diagrammatic, anterior-posterior view of a distal femur with an implanted exemplary augment in accordance with the present disclosure, having a configuration capable of attachment to a single, lateral epicondyle.

FIG. 3 is a diagrammatic, anterior-posterior view of an exemplary augment 160 implanted within a bone cavity 110. The augment 160 can be a lateral metaphyseal augment only (below the dashed line 152) or a metadiaphyseal augment. The augment 160 can be substantially similar in structure and function to the augment 100, 150, except for the distinctions noted herein. Rather than use for the medial side (FIG. 2), the augment 160 can be used for the lateral side of the patient. Same reference numbers are therefore used to refer to same structures. Rather than securing the augment 100 to both medial and lateral epicondyles, the augment 160 is configured for attachment to only the lateral epicondyle. Thus, the augment 160 defines a substantially L-shaped cross-section.

The augment 160 is attached to the lateral femoral epicondyles including the attached lateral collateral ligament. Once the augment 160 is attached and fixed to surrounding bone 102 and/or soft tissue, the stemmed femoral knee prosthesis can be inserted with or without bone cement. The dashed line 152 represents the line at which a partial metaphyseal augment 160 ends. FIG. 3 therefore shows both the partial (medial or lateral only) metaphyseal only augment 160, as well as the partial (medial or lateral) metaphyseal/diaphyseal augment 160. The augment 160 can be used where the bone 102 has healthy bone remaining on one side of the bone cavity 110, allowing for introduction and implantation of the augment 160 without removing the healthy bone. The augment 160 is secured to only one side (or along a partial radial edge) of the bone 102.

Figure 4:
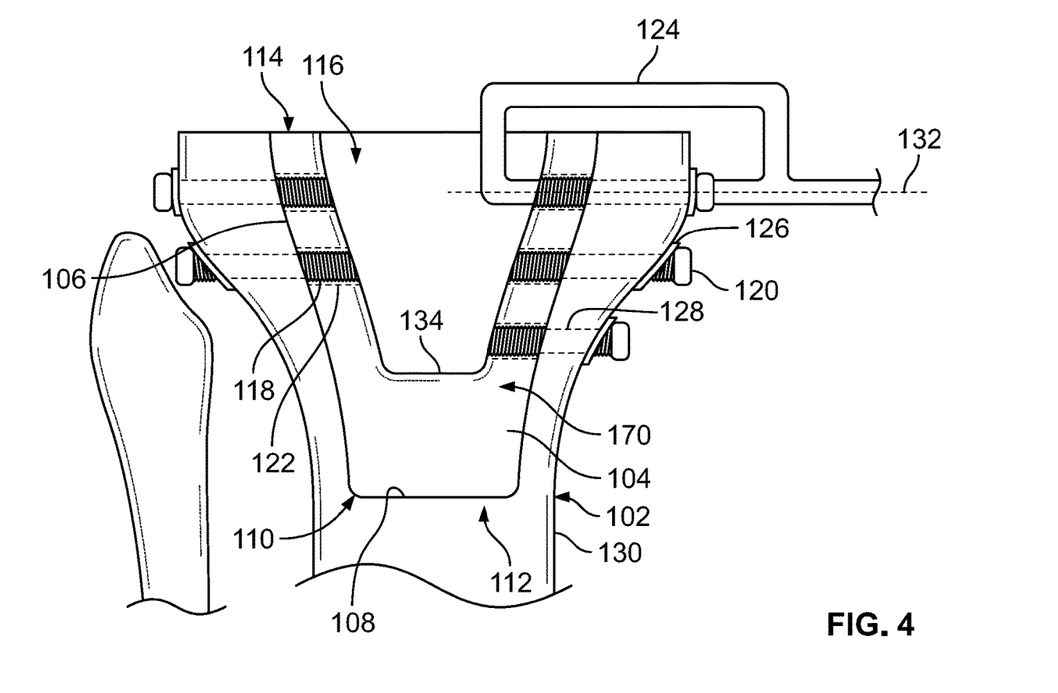
FIG. 4 is a diagrammatic, anterior-posterior view of a proximal tibia with an implanted exemplary augment in accordance with the present disclosure.
Figure 5:
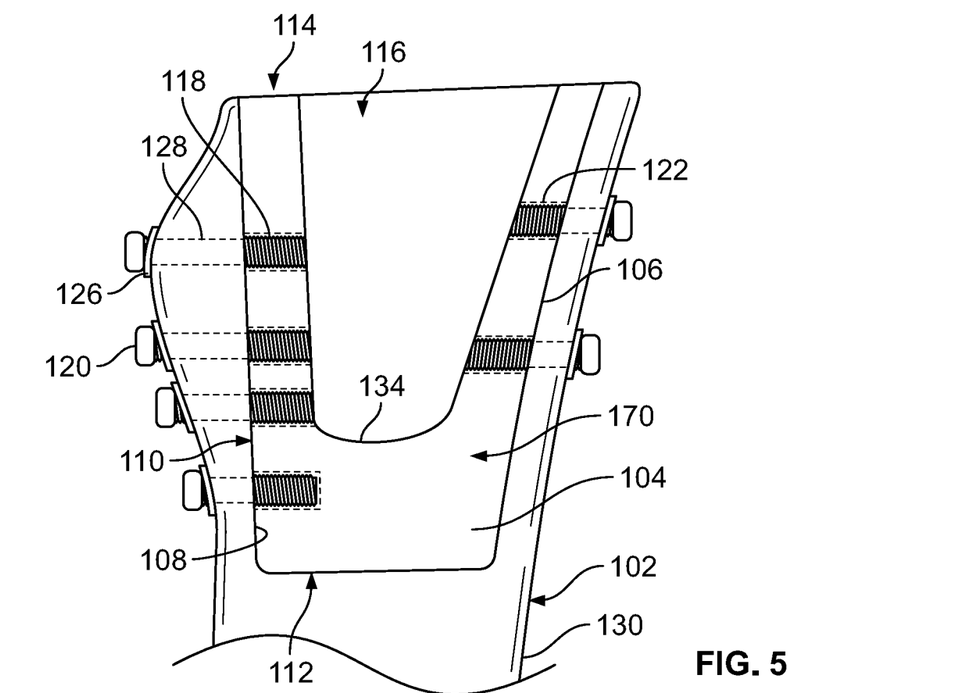
FIG. 5 is a diagrammatic, lateral view of a proximal tibia of FIG. 4 with an implanted exemplary augment in accordance with the present disclosure.

FIGS. 4 and 5 are diagrammatic, anterior-posterior and lateral views of an exemplary augment 170 implanted within a bone cavity 110 of a tibia bone 102. The augment 170 can be substantially similar in structure and function to the augment 100, except for the distinctions noted herein. Same reference numbers are therefore used to refer to same structures. Rather than fixation as a distal femoral augment (FIG. 1), the augment 170 can be used as a proximal tibial augment. The augment 170 is configured for tibial tubercle/patellar tendon insertion and attachment to the surrounding tibial bone 102 which is accessible medially, anteriorly and laterally. In some embodiments, the augment 170 can be used to attach the tibial tubercle with the patellar tendon. For example, the fasteners 120 can pass through the patellar tendon and attach the tibial tubercle into the threaded hole 118 of the augment 170. The augment 170 can define a substantially cone-shaped configuration with a squared off bottom surface 134. Once the augment 170 is attached and fixed to the surrounding bone 102 and/or soft tissue, the stemmed tibial knee prosthesis can be inserted with or without bone cement.

Figure 6:
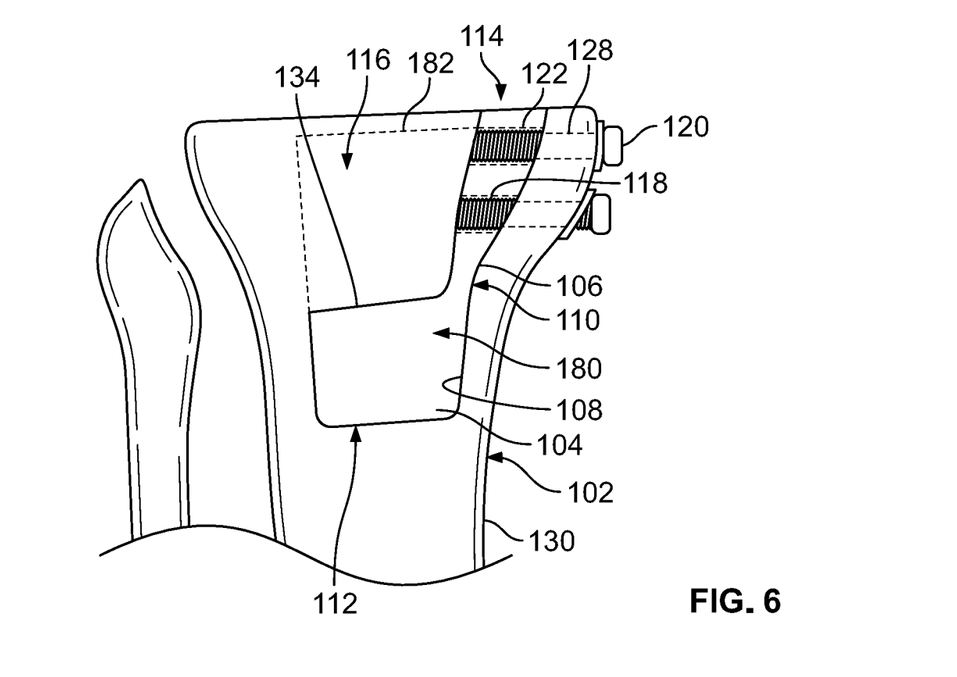
FIG. 6 is a diagrammatic, anterior-posterior view of a proximal tibia with an implanted exemplary augment in accordance with the present disclosure.
Figure 7:
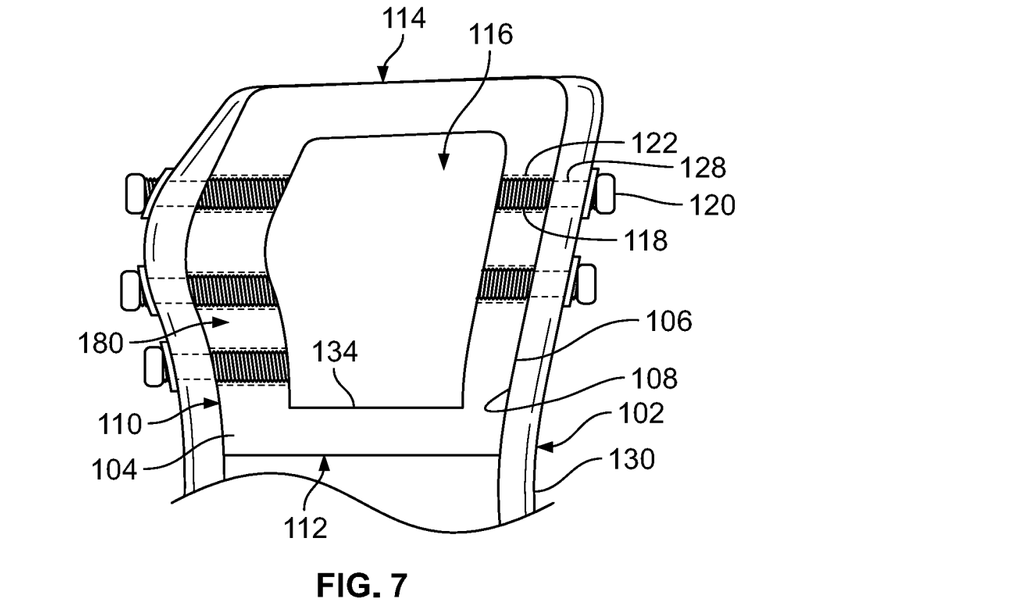
FIG. 7 is a diagrammatic, lateral view of a proximal tibia of FIG. 6 with an implanted exemplary augment in accordance with the present disclosure.

FIGS. 6 and 7 are diagrammatic, anterior-posterior and lateral views of an exemplary augment 180 implanted within a bone cavity 110 of a tibia bone 102. The augment 180 can be substantially similar in structure and function to the augment 100, except for the distinctions noted herein. Same reference numbers are therefore used to refer to same structures. The augment 180 is configured for tibial tubercle/patellar tendon insertion and attachment to the surrounding tibial bone 102. Fasteners 120 are used to enhance fixation.

The augment 180 can be used in instances of low bone loss or bone loss on only one side of the cavity 110. In some embodiments, in the lateral cross-sectional, the augment 180 can define a tapered, cylindrical configuration with a solid proximal end 114 enclosing the cavity 116. The dashed line 182 represents the anterior and posterior extension of the augment 180 with the hollow cavity 116 in the center. The augment 180 can allow for preservation of tibial bone stock in the setting of anterior or medial tibial bone loss, fracture or fragmentation. Once the augment 180 is attached and fixed to the surrounding bone 102 and/or soft tissue, the stemmed tibial knee prosthesis can be inserted with or without bone cement.

As noted above, the exemplary augments disclosed herein can be used for hip replacement surgery. For example, the augments can be attached to the acetabular or pelvic bone to supplement deficient bone structure. Fasteners can be used to attach the augment to the acetabular or pelvic bone. In some embodiments, fasteners can be used to attach the augment to custom acetabular components or acetabular reconstruction cages to provide additional support. Such augments can be used to set acute and chronic acetabular fractures or pelvic discontinuities, particularly those with advanced bone loss. The fasteners can provide enhanced fixation thereby increasing the surgeon's comfort in using more constrained acetabular components to limit dislocation in the setting of acetabular bone loss and soft tissue compromise where the risks of dislocation are increased.

Figure 8:
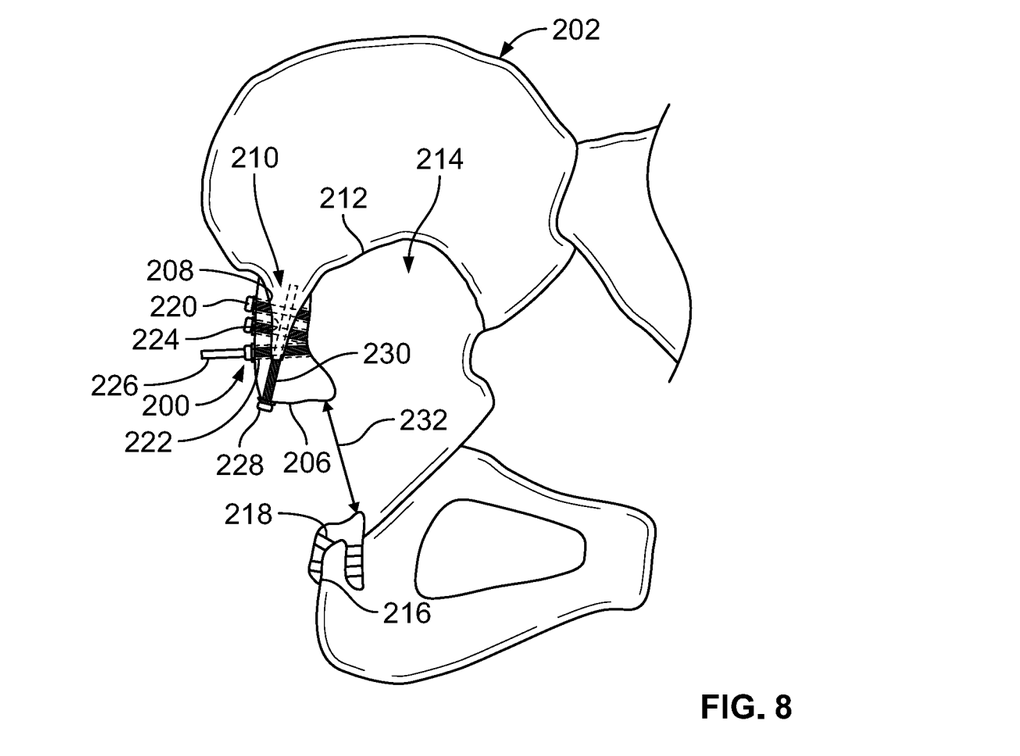
FIG. 8 is a diagrammatic, anterior-posterior view of an acetabulum with an implanted exemplary augment in accordance with the present disclosure.

FIG. 8 is a diagrammatic, anterior-posterior view of an exemplary augment 200 implanted in a bone 202 (e.g., an acetabulum). The augment 200 can be substantially similar in structure and function to the augment 100, except for the distinctions noted herein. The augment 200 includes a body 204 having a substantially U-shaped configuration. The augment 200 includes an outer surface 206 configured to face away from the bone 202 and an inner surface 208 defining a hollow inner cavity 210 configured to be in substantially direct contact with the bone 202. Particularly, the hollow inner cavity 210 can be configured and dimensioned to receive therein a protruding portion of the bone 202 such that the augment 200 receives and covers the protruding portion of the bone 202. One side of the augment 200 fits within and is positioned against the inner surface 212 of the bone cavity 214, while the opposing side of the augment 200 fits outside of the bone cavity 214 and against the outer surface 216 of the bone 202.

The augment 200 includes one or more holes 218 preformed therein and extending from the outer surface 206 into the hollow inner cavity 210. The holes 218 in the segments of the augment 200 on opposing sides of the bone 202 are respectively aligned for introduction of a fastener 220 therethrough. The holes 218 can be threaded to mate with threads of the fastener 220. In some embodiments, a deformable material 222 can surround unthreaded holes 218, the deformable material 222 capable of deforming due to introduction of the fastener through the hole 218.

During implantation, the bone cavity 214 can be cleaned and prepared for introduction of the augment 200. Holes 224 can be drilled in the bone 202 in a position corresponding with the holes 218 of the augment 200. In some embodiments, a drill guide 226 can be used to ensure alignment of the holes 218, 224. The augments 200 can be positioned on the bone 202 such that the holes 218, 224 are aligned. Each fastener 220 is first threaded through the hole 218 of the augment 200 at the outer surface 216 of the bone 202, passed through the hole 224 in the bone 202, and further threaded into the hole 218 of the augment 200 in the bone cavity 214.

The fasteners 220 thereby secure the augment 200 to the protruding portion of the bone 202 to correct for bone loss in the area. In some embodiments, an additional fastener 228 (e.g., a locking or non-locking screw) can be threaded through a hole 230 in the augment 200 and into the bone 202. The fastener 228 can pass substantially perpendicularly to the fasteners 220. In some embodiments, after the area of bone loss has been at least partially by the implantation of the augments 200, an acetabular shell (not shown) can be implanted in the space 232 between the augments 200.

The augment 200 of FIG. 8 can therefore be used in instances of bone loss involving the acetabular dome and medial acetabular wall. The U-shaped porous augment 200 includes holes or slots in both the medial and lateral aspects of the body with fasteners extending from the lateral augment 200 through the ilium and into the threaded portion of the medial augment 200. It should be understood that the bottom portion of the U-shaped augment 200 can be oriented superiorly if the augment 200 is flipped for use in the setting of ischial bone loss.

Figure 9:
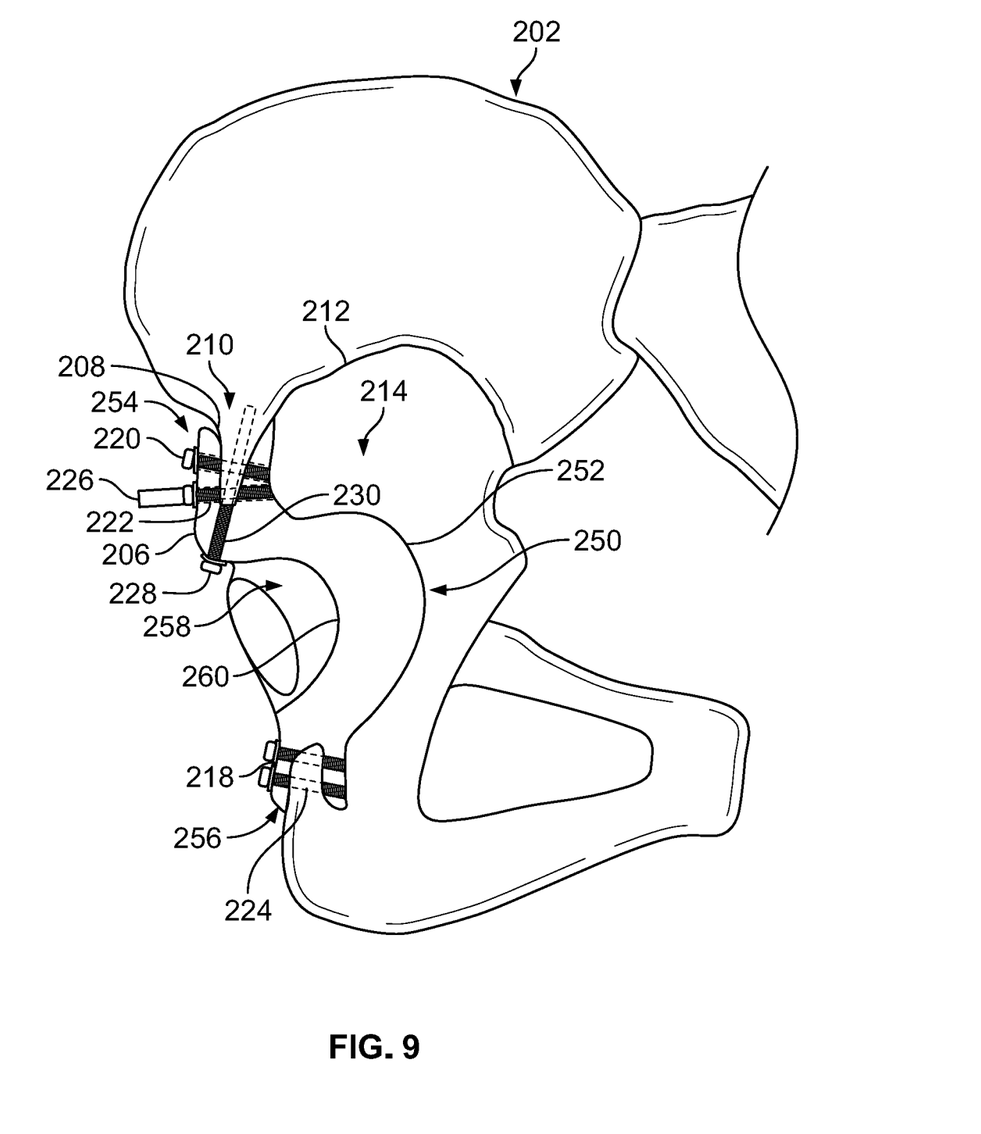
FIG. 9 is a diagrammatic, anterior-posterior view of an acetabulum with an implanted exemplary augment in accordance with the present disclosure.

FIG. 9 is a diagrammatic, anterior-posterior view of an exemplary augment 250 implanted in a bone 202 (e.g., an acetabulum). The augment 250 can be substantially similar in structure and function to the augment 200, except for the distinctions noted herein. Same reference numbers are therefore used to refer to same structures. Rather than having a space 232 between the augments 200, the augment 250 can include a porous cup or cage portion 252 integrally formed with the end sections 254, 256 that fixate the augment 250 to the bone 202. The end sections 254, 256 can be substantially similar in structure and function to the augment 200, and connect to the centrally disposed portion 252. In some embodiments, a liner 258 can be disposed on the curved (e.g., concave) surface 260 of the portion 252.

The bone 202 of FIG. 9 is shown with a typical up and in pattern of bone loss involving the acetabular dome and medial acetabular wall in combination with a pelvic discontinuity. A customized augment 250 can be used as shown in FIG. 9 to bridge the area of bone loss. The augment 250 can be fixated to the bone 202 using fasteners 220, the fasteners 220 extends from the lateral aspect of the porous coated ilium flange (e.g., augment 250) into the host bone 202 and back into the medial porous coated portion of the augment 250. In some embodiments, the augment 250 can be formed from a single, fully porous material (e.g., a porous metal, a porous non-metal, a porous biocompatible material, or the like). In some embodiments, the augment 250 can be formed from one or more materials (e.g., a porous coating sprayed on or fixed to a solid metal substrate) The augment 250 can also be fixated into the distal ischium in the setting of bone loss. In some embodiments, the liner 258 can be cemented into the cage or custom cup portion 252 in the desired orientation.

Figure 10:
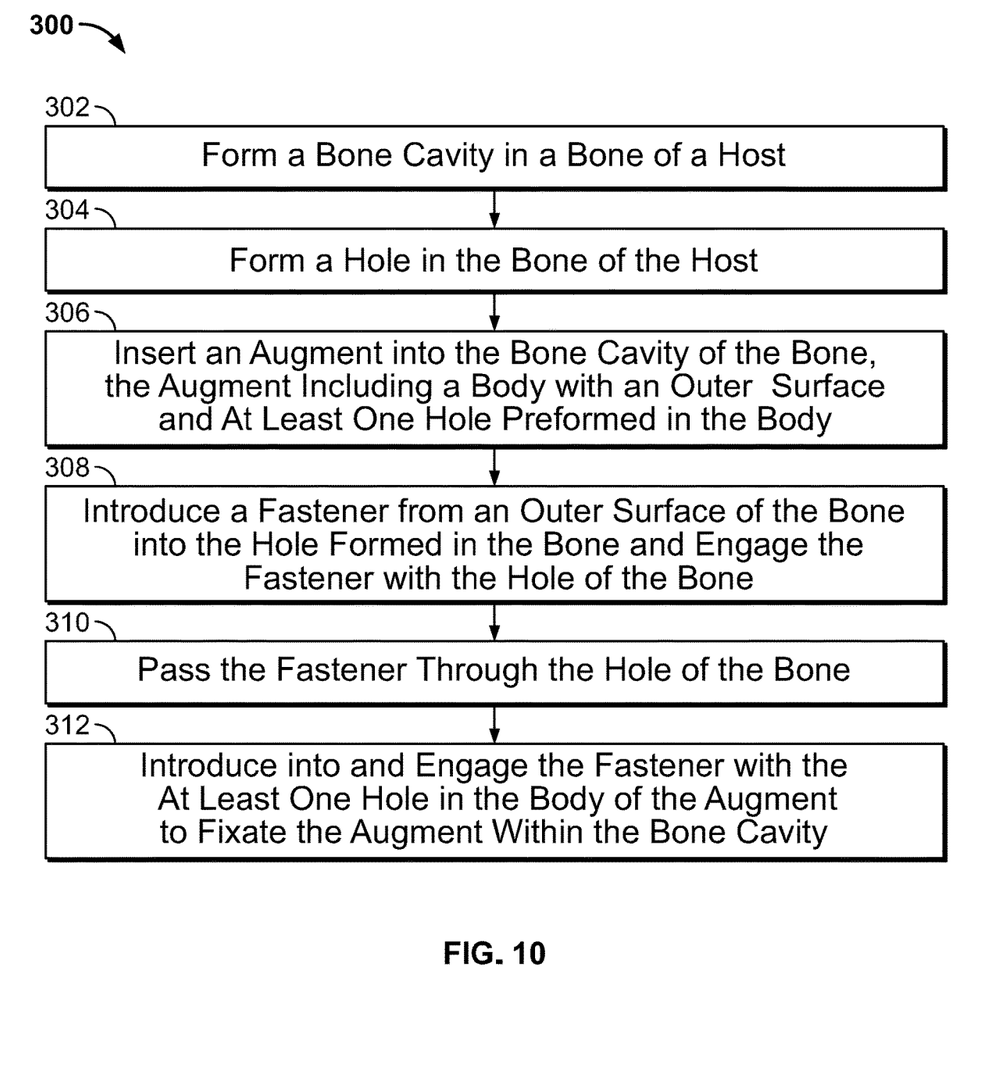
FIG. 10 is a flowchart illustrating an exemplary process of implanting an augment in accordance with the present disclosure.

FIG. 10 is a flowchart illustrating an exemplary process 300 of implanting the augments discussed herein. To begin, at step 302, a bone cavity can be formed or cleaned in the bone of a host. At step 304, a hole in the bone of the host can be formed in preparation for implantation and attachment of the augment. At step 306, the augment is at least partially inserted into the bone cavity of the bone. The augment includes a body with an outer surface and at least one hole preformed in the body. The preformed hole in the augment can be aligned with the hole in the bone. At step 308, a fastener can be introduced from an outer surface of the bone into the hole formed in the bone, and engaged with the hole of the bone. At step 310, the fastener can be passed through the hole of the bone. At step 312, the fastener is introduced into and engaged with the hole in the body of the augment to fixate the augment within the bone cavity.

The exemplary augments can therefore be customized to fit into bone cavities of different configurations to prevent unnecessary removal of healthy bone. Fixation of the augment with a fastener extending from the outer surface of the bone ensures that the augment is pulled into direct or substantially direct contact with the inner surface of the bone cavity, resulting in improved bone in-growth over time.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A method of implanting an augment, comprising:
    inserting the augment into a bone cavity of a bone of a host, the augment including a body with an outer surface and at least one hole preformed in the body;
    introducing a fastener from an outer surface of the bone into a hole formed in the bone and engaging the fastener with the hole of the bone;
    passing the fastener through the hole of the bone; and
    introducing into and engaging the fastener with the at least one hole in the body of the augment to fixate the augment within the bone cavity.

2. The method of claim 1, comprising forming the bone cavity in the bone of the host.

3. The method of claim 1, comprising forming the hole in the bone, the hole extending from the outer surface of the bone into the bone cavity.

4. The method of claim 1, wherein engaging the fastener with the at least one hole in the body of the augment fixates the augment to an inner surface of the bone cavity.

5. The method of claim 1, wherein the bone is at least one of a femur, a tibia, or an acetabulum.

6. The method of claim 1, wherein the augment is formed from at least one of a metal, a non-metal, or a biodegradable material.

7. The method of claim 1, wherein the body of the augment is porous.

8. The method of claim 1, wherein the body is flexible.

9. The method of claim 1, wherein the augment is conical in shape including a hollow inner cavity.

10. The method of claim 9, wherein the at least one hole in the body of the augment extends from the outer surface to the hollow inner cavity.

11. The method of claim 1, wherein the at least one hole in the body of the augment is threaded, and the method comprises engaging threads of the fastener with complementary threads of the at least one hole in the body of the augment.

12. The method of claim 1, wherein at least a portion of the body of the augment comprises a deformable material, the at least one hole preformed in the deformable material of the augment.

13. The method of claim 12, wherein the augment comprises the deformable material in an area immediately surrounding the at least one hole of the augment.

14. The method of claim 12, wherein engaging the fastener with the at least one hole in the body of the augment comprises deforming the deformable material of the augment with threads of the fastener to fixate the fastener to the augment.

15. A method of implanting an augment, comprising:
    forming a bone cavity in a bone of a host;
    forming a hole in the bone, the hole extending from an outer surface of the bone into the bone cavity;
    inserting the augment into the bone cavity of the bone, the augment including a body with an outer surface and at least one hole preformed in the body;
    introducing a fastener from the outer surface of the bone into the hole of the bone and engaging the fastener with the hole of the bone;
    passing the fastener through the hole of the bone; and
    introducing into and engaging the fastener with the at least one hole in the body of the augment to fixate the augment within the bone cavity.

\* \* \* \* \*